United States Patent [19]

Carvalho et al.

[11] Patent Number: 5,556,968
[45] Date of Patent: Sep. 17, 1996

[54] POLYAZAMACROCYCLE CHELATING AGENTS WITH AMIDE LINKAGES

[75] Inventors: Joan F. Carvalho, Mountainview; Shaun P. Crofts, Santa Clara; John Varadarajan, Sunnyvale, all of Calif.

[73] Assignee: Nycomed Salutar, Inc., Sunnyvale, Calif.

[21] Appl. No.: 50,249

[22] PCT Filed: Nov. 6, 1991

[86] PCT No.: PCT/EP91/02118

§ 371 Date: Feb. 22, 1994

§ 102(e) Date: Feb. 22, 1994

[87] PCT Pub. No.: WO92/08707

PCT Pub. Date: May 29, 1992

[30] Foreign Application Priority Data

Nov. 7, 1990 [GB] United Kingdom ............... 9024208

[51] Int. Cl.⁶ .................. C07D 245/02; C07D 259/00; A61K 49/00
[52] U.S. Cl. .................. 540/460; 540/450; 540/474; 424/9.3; 534/15
[58] Field of Search .................. 540/460, 452, 540/450, 414; 514/183, 185; 424/9.3

[56] References Cited

U.S. PATENT DOCUMENTS

| 3,723,087 | 3/1973 | Chapp | 71/92 |
| 4,999,349 | 3/1991 | Toda et al. | 540/460 |
| 5,025,023 | 9/1989 | Konishi et al. | 540/460 |
| 5,132,409 | 7/1992 | Felder et al. | 540/452 |
| 5,194,605 | 3/1993 | Greenlee et al. | 540/460 |

FOREIGN PATENT DOCUMENTS

| 250358 | 12/1987 | European Pat. Off. |
| 0255471 | 2/1988 | European Pat. Off. |
| 0287465 | 10/1988 | European Pat. Off. |
| 0413405 | 2/1991 | European Pat. Off. |
| 165728 | 12/1985 | Japan |
| 0130592 | 9/1990 | Japan |
| 9024208 | 11/1990 | United Kingdom |

*Primary Examiner*—Mukund J. Shah
*Assistant Examiner*—P. K. Sripada
*Attorney, Agent, or Firm*—Fish & Richardson P.C.

[57] ABSTRACT

Macrocyclic chelating agents, optionally possessing more than one macrocyclic ring having at least two peptide linkages within the macrocyclic skeleton. The chelating agents are used for the preparation of paramagnetic metal chelates for use as MRI contrast agents.

9 Claims, No Drawings

POLYAZAMACROCYCLE CHELATING AGENTS WITH AMIDE LINKAGES

FIELD OF THE INVENTION

The present invention relates to certain novel macrocyclic chelating agents, in particular derivatised polyamines, and to their uses, especially their medical uses.

BACKGROUND OF THE INVENTION

The medical use of chelating agents is well established, for example as stabilizers for pharmaceutical preparations, as antidotes for poisonous heavy metal species and as diagnostic agents for the administration of metal species (e.g. ions or atoms) for diagnostic techniques such as X-ray, magnetic resonance imaging (MRI) or ultrasound imaging or scintigraphy.

Polyamine chelating agents, for example aminopoly(carboxylic acid or carboxylic acid derivative) (hereinafter APCA) chelating agents and their metal chelates, are well known and are described for example in U.S. Pat. No. 2,407,645 (Bersworth), U.S. Pat. No. 2,387,735 (Bersworth), EP-A-71564 (Schering), EP-A-130934 (Schering), EP-A-165728 (Nycomed AS), DE-A-2918842 (Rexolin Chemicals AB), DE-A-3401052 (Schering), EP-A-258616 (Salutar), DE-A-3633245 (Schering) EP-A-263059 (Schering), EP-A-277088 (Schering) and DE-A-3633243 (IDF).

Thus, for example, EP-A-71564 describes paramagnetic metal chelates, for which the chelating agents are nitrilotriacetic acid (NTA), N,N,N',N'-ethylenediaminetetraacetic acid (EDTA), N-hydroxyethyl-N,N',N'-ethylenediaminetriacetic acid (HEDTA), N,N,N',N'',N''-diethylenetriaminepentaacetic acid (DTPA) and N-hydroxyethyliminodiacetic acid, as being suitable as contrast agents for MRI, contrast being achieved by the effect on surrounding solvent protons of the magnetic field of the paramagnetic species (e.g. Gd(III)), with the chelating agents serving to reduce the toxicity and to assist administration of that paramagnetic species. Amongst the particular metal chelates disclosed by EP-A-71564 was GdDTPA, the use of which as an MRI contrast agent has recently received much attention. The Gd(III) chelate of 1,4,7,10-tetraazacyclododecanetetraacetic acid (DOTA), referred to in DE-A-3401052 (Schering) and in U.S. Pat. No. 4,639,365 (University of Texas), has also recently received attention in this regard.

To improve stability, water solubility and selectivity, relative to the APCA chelating agents described in EP-A-71564, Schering, in EP-A-130934, have proposed the partial substitution for the N-attached carboxyalkyl groups of alkyl, alkoxyalkyl, alkoxycarbonylalkyl or alkylaminocarbonylalkyl groups, where any amide nitrogens may themselves carry polyhydroxyalkyl groups. More recently, to improve compatibility, stability, solubility and selectivity, in EP-A-250358 Schering have proposed a narrow range of compounds having a DTPA-like structure including a bridging alkylene chain.

In the field of hepatobiliary MRI contrast agents, where lipophilicity rather than hydrophilicity is desired, Nycomed in EP-A-165728, have proposed the use of paramagnetic chelates of certain anilide group-containing iminodiacetic acids and Lauffer in WO-A-86/06605 has suggested the use of paramagnetic chelates of triaza and tetraaza macrocycles which carry a fused aromatic ring but are otherwise unsubstituted.

Nycomed, in EP-A-299795, suggest that the toxicity of certain APCA chelating agents and their chelates may be reduced by introducing at least one hydrophillic moiety as a substituent on one or more of the alkylene bridges between the amine nitrogens.

However, all hitherto known APCA chelating agents and their metal chelates encounter problems of toxicity, stability or selectivity and there is thus a general and continuing need for such polyamine chelating agents which form metal chelates of reduced toxicity, improved stability or improved water solubility. In particular there is perceived to be a need for chelants which form highly stable metal chelates which can be used to produce low osmolality contrast media.

SUMMARY OF THE INVENTION

We now propose a novel class of macrocyclic polyamine chelating agents which incorporate at least two peptide linkages within the macrocyclic skeleton.

Thus viewed from one aspect the present invention provides a compound of formula I

(wherein $L^1$ represents a bond or an optionally unsaturated $C_{2-14}$ hydrocarbon chain optionally substituted by groups selected from $R^2$, $R^3$ and $R^4$, optionally having chain backbone methylene moieties which are separated by at least 2 ring carbon atoms from ring heteroatoms replaced by oxygen or sulphur atoms or $NA'$ groups, optionally carrying a fused 5–8 membered saturated or unsaturated carbocyclic or heterocyclic ring itself optionally substituted by groups selected from $R^2$, $R^3$ and $R^4$, and optionally carrying a fused macrocyclic ring of formula Ia

where $L^1$ and $L^3$ share at least two common ring atoms and optionally an unsaturated ring bond and $L^3$ is as defined for $L^1$ but may not itself carry a further fused macrocycle of formula Ia;

$L^2$ represents a group of formula $[(CR^2R^3)_nX]_m(CR^2R^3)_n$ optionally having a moiety $[(CR^2R^3)_nX]_2(CR^2R^3)_n$ replaced by a moiety $(CR^2R^3)_{n-1}CONR^1$—$L^4$—$NR^1CO(CR^2R^3)_{n-1}$ where $L^4$ is a group $L^1$ but may not carry a fused macrocycle of formula Ia;

$R^4$ groups on separate L groups together represent a group of formula Ib

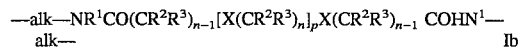

where alk is a group $L^1$ but may not carry a fused macrocycle of formula Ia or a substituent $R^4$;

each $R^1$ independently represents a group $R^5$ or $X^2R^5$ where $X^2$ represents an oxygen or sulphur atom or a group $NR^5$ and each $R^5$ independently represents a hydrogen atom or an alkyl or aryl group optionally substituted by a group Y;

each X independently represents an oxygen or sulphur atom or, preferably, a group of formula NA;

each A independently represents a hydrogen atom or an alkyl group optionally substituted by a group Y;

each A' independently represents a group A or a group $R^4$;

each Y independently represents a group Z, COZ, $SO_2Z$, $POZ_2$, $CON(OR^6)R^6$ or CSZ;

each Z independently represents a group $OR^6$, $SR^6$ or $NR_2^6$;

each $R^6$ independently represents a hydrogen atom or an alkyl group optionally carrying at least one substituent selected from hydroxyl and alkoxy groups, or $NR_2^6$ together represents a nitrogen-attached 5–7 membered saturated heterocyclic ring optionally containing as a further ring heteroatom a nitrogen, oxygen or sulphur atom and optionally substituted by one or more $R^7$ groups;

each $R^7$ independently represents a halogen atom, a hydroxy or sulphonate group or an alkyl or alkoxy group optionally carrying at least one or more hydroxy, alkoxy or hydroxyalkyl groups;

each $R^2$ and $R^3$ independently represents a hydrogen atom or an aryl or alkyl group optionally carrying at least one substituent selected from aryl and Y groups, or two groups A and/or $R^3$ attached at different positions on a macrocyclic ring may together with the intervening macrocyclic ring atoms form a 5–8, preferably 5 or 6, membered saturated or unsaturated heterocyclic or carbocyclic ring, itself optionally substituted by one or more $R^7$ groups;

m is an integer of 0–8, preferably 1–6;

n is an integer of 2–5, preferably 2, 3, or 4, especially preferably 2;

p is an integer of 0–8, preferably 1–6;

with the proviso that at least 2, preferably at least 3, ionizable Y groups are present;

wherein each alkyl or alkylene moiety unless otherwise specified contains from 1 to 8 carbon atoms, each aryl moiety contains 5 to 12 ring atoms and each heterocyclic moiety unless otherwise specified contains nitrogen, oxygen or sulphur atoms as rings heteroatoms)

or a chelate complex or salt thereof.

Viewed from a further aspect the invention also provides a compound for use a therapeutic or diagnostic agent, e.g. as a contrast agent, a detoxification agent or a radiotherapeutic agent, said compound being a compound of formula I or a chelate complex or salt thereof.

DETAILED DESCRIPTION OF THE INVENTION

In the compounds of the invention, alkyl or alkylene moieties in groups A, alk, $L^1$, $L^2$, $L^3$, $L^4$, $R^1$, $R^2$, $R^3$, $R^4$, $R^5$, $R^6$ and $R^7$ unless otherwise stated may be straight-chained or branched and preferably contain from 1 to 6, and most preferably 1 to 4, carbon atoms. Aryl moieties unless otherwise stated preferably comprise phenyl or naphthyl rings.

Where groups may optionally be substituted by hydroxyl or alkoxy groups, this may be monosubstitution or polysubstitution and, in the case of polysubstitution, alkoxy and/or hydroxyl substituents may be carried by alkoxy substituents.

Where, as is particularly preferred, the compounds of the invention incorporate one or more hydrophilic groups (for example as or pendent from the backbone structures of A, alk, $L^1$, $L^2$, $L^3$, $L^4$, $R^1$, $R^2$, $R^3$, $R^4$, $R^5$, $R^6$ and $R^7$ groups), these are preferably hydroxyl groups or straight-chained or branched hydrocarbon moieties having a carbon atom content of from 1 to 8, especially preferably 1 to 6, carbon atoms. The hydrophilic groups may be alkoxy, polyalkoxy, hydroxyalkoxy, hydroxypolyalkoxy, polyhydroxyalkoxy, polyhydroxylated polyalkoxy, hydroxyalkyl, polyhdyroxyalkyl, alkoxyalkyl, polyalkoxyalkyl, hydroxylated alkoxyalkyl, polyhydroxylated alkoxyalkyl, hydroxylated polyalkoxyalkyl, or polyhydroxylated polyalkoxyalkyl groups. More preferably however they will generally be monohydroxyalkyl or polyhydroxyalkyl groups. The hydrophilic groups serve to increase the hydrophilicity and reduce the lipophilicity of the metal chelates formed with the chelating agents of the invention and it is preferred that the compounds of formula I should contain at least 1, conveniently from 1 to 4, and preferably 1, 2 or 3 such hydrophilic groups. As such hydrophilic groups, the compounds of the invention may thus include for example hydroxy-methyl, 2-hydroxyethyl, 2-hydroxypropyl, 1,2-dihydroxyethyl, 3-hydroxypropyl, 2,3-dihydroxypropyl, 2,3,4-trihydroxybutyl, 1-(hydroxymethyl)-2-hydroxy-ethyl, methoxymethyl, ethoxymethyl, 2-hydroxyethoxy-methyl, methoxyethoxymethyl, (2-hydroxy-ethoxy)ethyl, etc., groups.

Compounds of formula I containing non-hydrophilic groups pendant from the macrocyclic skeleton, e.g. hydrogen or unsubstituted lower alkyl, e.g. $C_{1-4}$ alkyl, are also preferred, especially where $R^6$ is hydrogen and an $R^2$ is unsubstituted lower alkyl, e.g. methyl or ethyl.

It is also especially preferred that groups X comprising no ionizing group Z should be non-adjacent and particularly that they should be at approximately opposed positions on the macrocyclic skeleton.

The compounds of formula I according to the invention particularly preferably contain one, two or three macrocyclic rings and, within those, two or three pairs of peptide linkages. In particular the chelant compounds of formula I are preferably monomacrocyclic diamides, monomacrocyclic tetraamides, bimacrocyclic tetraamides or bimacrocyclic hexaamides. Chelants having such structures may be used to chelate one or more, especially preferably two or three, metal ions as the ability of a chelant to chelate more than one metal ion simultaneously has the clear advantage that it can be used to produce reduced osmolality diagnostic or therapeutic agents.

In the chelant compounds of formula I the linker moieties $L^1$, $L^2$, $L^3$ and $L^4$ are preferably $C_{2-10}$ alkylene, alkenylene, alkynylene, oxaalkylene or azaalkylene chains optionally carrying pendant alkyl or hydrophilic groups or fused homocyclic or heterocyclic rings (or in the case of $L^1$, fused macrocyclic ring).

Examples of suitable hydrophilic substituents are listed above. Examples of fused homocyclic or heterocyclic rings include benzene, pyridine, pyrrole, furan, pyrazine, piperidine, piperazine, pyrrolidine and morpholine rings. Where $L^1$ caries a fused macrocyclic ring the common ring skeletal section is preferably a $C_{2-4}$ alkanetetrayl or alkenetetrayl moiety, especially an ethanetetrayl or ethenetetrayl moiety, and the groups $L^2$ in each of the macrocyclic rings are preferably identical or substantially similar, e.g. each may represent a $(CH_2)_2[NA(CH_2)_2]_qNA(CH_2)_2$ group where q is 0 or 1.

Particularly preferred compounds of formula I also include the bimacrocyclic hexaamides in which $L^1$ and $L^2$ are linked by a group of formula Ib. In such compounds the branching sites in the L groups are conveniently carbon or nitrogen atoms, preferably separated from the adjacent peptide nitrogens by at least two positions on the macrocycle skeleton, or fused homocyclic or heterocyclic rings, preferably separated from the adjacent peptide nitrogens by at least one position on the macrocycle skeleton.

Thus particular examples of the L groups include the following:

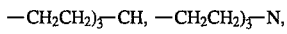

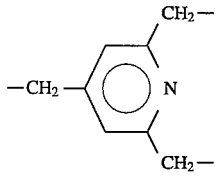

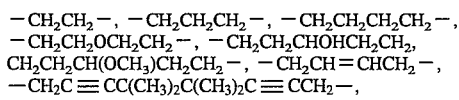

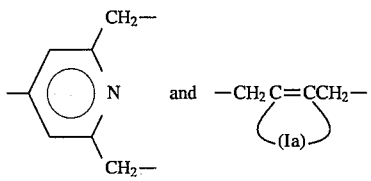

where for the first three groups one terminal $CH_2$ group is part of an alk moiety of formula Ib and where for the last group (Ia) indicates that a fused macrocycle of formula Ia is attached as indicated.

In general, in monomacrocyclic diamide chelants of formula I, in the $L^2$ moiety m is preferably 0, 1, 2 or 3. In monomacrocyclic tetraamides, $L^2$ preferably comprises two identical or substantially similar moieties of formula $[(CR^2R^3)_nX]_r$ (where r is 0, 1 or 2) on either side of the central bisamide group and $L^4$ is preferably identical to $L^1$. Similarly in bimacrocyclic hexaamides the three bridging chains are preferably identical or substantially similar and preferably comprise $(CH_2)NA[(CH_2)_2NA]_s(CH_2)$ (where s is 2, 3 or 4) chains attached at each end to peptide carbonyl groups.

Particularly preferred compounds of formula I include those of formulae Ic, Id, Ie and If

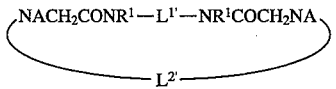

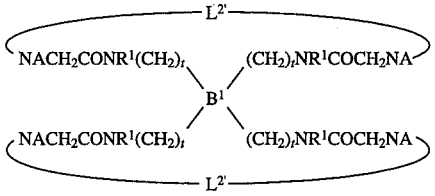

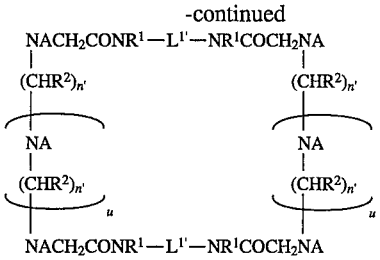

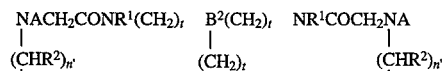

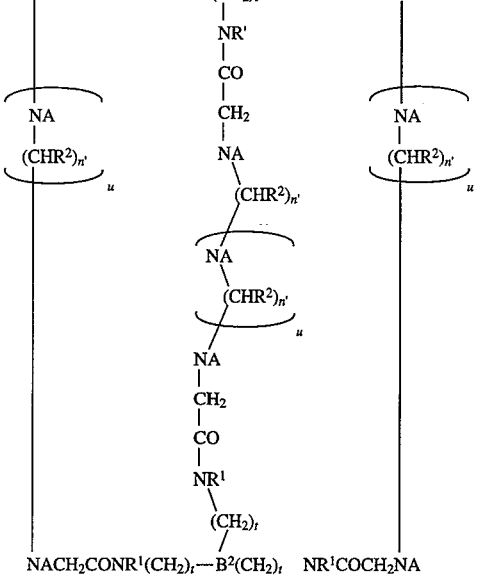

where $L^{1'}$ is a $C_{2-10}$ alkylene, alkenylene, alkynylene, oxaalkylene or azaalkylene group optionally substituted by a hydrophillic group and optionally carrying a fused 5 or 6 membered saturated or unsaturated homo- or heterocyclic ring which ring if heterocyclic contains one or two non-adjacent ring heteroatoms selected from O, N and S;

$L^{2'}$ is a group of formula $[(CHR^2)_{n'}X]_m(CHR^2)_{n'}$;

each n' is 2 or 3;

each t is 1, 2 or 3;

each u is 0, 1 or 2;

$B^1$ is a quadrivalent branching group selected from alkanetetrayl and alkenetetrayl groups and carbon-attached 6-membered saturated or unsaturated homo or heterocyclic rings which rings if heterocyclic contain one or two non-adjacent ring heteroatoms selected from O, N and S;

$B^2$ is a trivalent branching group selected from $CR^2$, N and carbon attached 6-membered saturated or unsaturated homo or heterocyclic rings which rings if heterocyclic contain one, two or three non-adjacent ring heteroatoms selected from O, N and S;

each $R^2$ is independently hydrogen or an alkyl group optionally carrying at least one Z substituent;

and X, A, m and $R^1$ are as hereinbefore defined.

Especially preferred compounds of formula I include those of formulae Ic wherein $L^{1'}$ is a 4,4,5,5-tetramethylocta-2,6-diynediyl, ethylene, trimethylene, tetramethylene, or but-2-enediyl group optionally substituted by a hydrophillic group, each X is NA and m is 1, 2 or 3; those of formula Id wherein m is 1, 2 or 3, each X is NA, t is 1 and $B^1$ is an ethanetetrayl or ethenetetrayl group; those of formula Ie where $L^{1'}$ is an ethylene, trimethylene or tetramethylene group or a group of formula

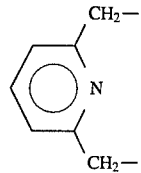

optionally substituted by a hydrophillic group; and those of formula If where t is 1 and $B^2$ is a group of formula $N(CH_2)_3$ or $CH(CH_2)_3$ or a pyrid-2,4,6-triyl group.

In the compounds of formulae I, Ic, Id, Ie and If, it is preferred that substituents A on macrocyclic ring nitrogens be hydrogen atoms or hydrophilically substituted $C_{1-3}$ alkyl groups, especially hydroxypropyl and more especially carboxymethyl groups or esters or amides thereof. For coordination of trivalent metal ions, such as Gd(III), Eu(III), Dy(III), Ho(III) and Yb(III) it is particularly preferred that the chelating compound should contain a multiple of 3 ring-nitrogen attached carboxymethyl groups, especially 3, 6 or 9, particularly preferably disposed in moieties $(CHR^2)_{n-1}$ $[N(CH_2COOH)(CHR^2)_n]_2$ $N(CH_2COOH)(CHR^2)_{n-1}$ attached at each end to peptide carbonyls.

It is also preferred that groups $R^1$ in the compounds of the invention be hydrogen atoms or alkyl or alkoxy groups.

Where a group $NR_2^6$ in a compound according to the invention is a nitrogen attached heterocyclic ring, it will conveniently be of formula

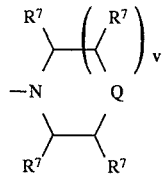

where v is 0, 1 or 2, and Q is $CHR^7$, $NR^4$, O or S, where v is zero Q preferably being $CHR^7$, Particularly preferably such groups are of formula

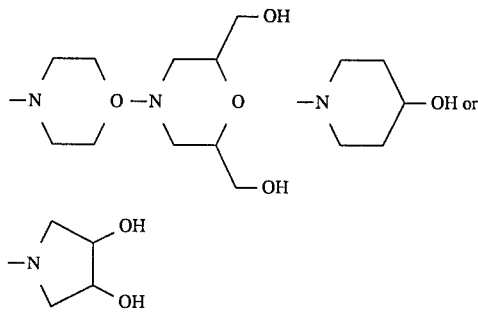

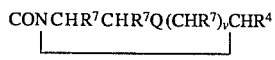

In the compounds of formula I, the groups Y preferably represent carboxylic acid or amide groups, for example groups of formula COOH, $CONH^2$, $$CONCHR^7CHR^7Q(CHR^7)_vCHR^4$$

(especially morpholine groups in which Q is oxygen and v is 1), $CONHR^6$ or $CONR_2^6$ (especially where $R^6$ is an alkyl or mono or polyhydroxyalkyl group, for example a $C_{1-6}$ alkyl group optionally carrying 1, 2, 3 or 4 hydroxyl groups).

Where Y is a carboxyl group, the compounds of formula I can conveniently form salts or chelates in which Y represents —COOM (where $M^+$ is a monovalent cation or a fraction of a polyvalent cation, for example an ammonium or substituted ammonium ion or a metal ion, for example an alkali metal or alkaline earth metal ion). Particularly preferably, $M^+$ is a cation deriving from an organic base, for example meglumine or lysine. In such salts or chelates one or more (but not necessarily all) of the carboxyl groups are transformed into COOM groups.

The chelant compounds of the invention find particular use as chelating agents for heavy metal ions, in particular ions useful in diagnostic imaging or in radiotherapy. Chelates of such ions and salts of charged chelate complexes fall within the scope of the present invention. However, to increase the biotolerability of such chelate compounds it is particularly preferred that the number of the ion-forming groups Y in the compounds of formula I be chosen to equal the valency of the metal species to be chelated by the compound of formula I. Thus, for example, where Gd(III) is to be chelated, the compound of formula I (or salt thereof) preferably contains a multiple of three ion-forming Y groups, for example —COOH (or —COOM). In this way, the metal chelate will be formed as a neutral species, a form preferred since the osmolalities in concentrated solutions of such compounds are low and since their toxicities relative to their ionic analogues are generally significantly reduced.

Included amongst the particularly preferred compounds according to the invention are those of formulae Ic to If wherein each $R^2$ represents a hydrogen atom or an optionally mono- or poly-hydroxylated, optionally mono- or poly-alkoxylated alkyl group, each Y represents a group of formula COZ or Z and Z represents a hydroxyl group or a group $SR^6$, $NR_6^2$, or $NHR^6$, and metal chelates and salts thereof.

Especially preferred compounds according to the invention include those of formulae Ig, Ih and Ij

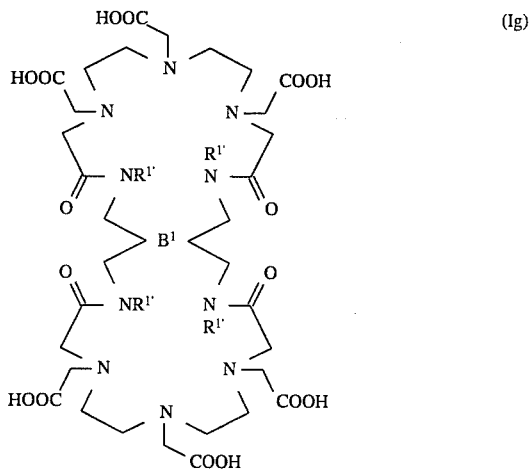

(Ig)

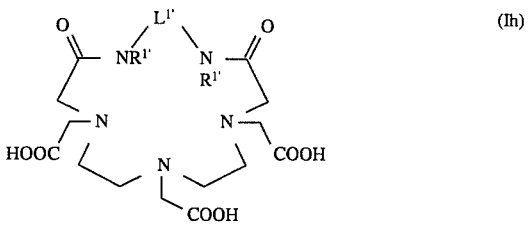

(Ih)

-continued

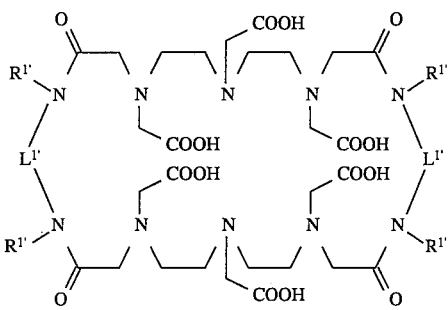

(Ij)

(where $R^{1'}$ is H, alkyl, or alkoxy or aryloxy; $L^{1'}$ is a 4,4,5,5-tetramethylocta-2,6-diynediyl, ethylene, trimethylene, tetramethylene, or but-2-enediyl group optionally substituted by a hydrophillic group; $B^1$ is >CH—CH< or >C=C< and $L^{1''}$ is an ethylene, trimethylene or tetramethylene group or a group of formula

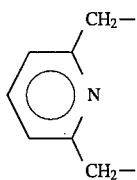

optionally substituted by a hydrophillic group) and the metal chelates and salts and esters thereof.

Viewed from a further aspect, the invention also provides a process for the preparation of the compounds of the invention, said process comprising one or more of the following steps:

(a) reacting a compound of formula II

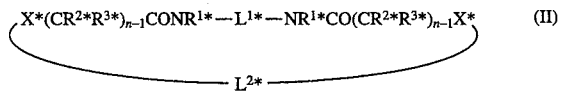
(II)

(wherein $X^*$, $R^{1*}$, $R^{2*}$, $R^{3*}$, $L^{1*}$ and $L^{2*}$ are as defined for X, $R^1$, $R^2$, $R^3$, $L^1$ and $L^2$ or are protected X, $R^1$, $R^2$, $R^3$, $L^1$ and $L^2$ groups with the proviso that at least one $X^*$ group or X group in $L^{1*}$ or $L^{2*}$ is of formula NH) with a compound of formula III Lv—A"  (III)

(wherein A" is a group A (other than hydrogen) or a protected A group and Lv is a leaving group for example a halogen atom, e.g. bromine or chlorine, or a tosylate group) and if necessary subsequently removing any protecting groups used;

b) reaction a compound of formula IV $LvCO(CR^{2*}R^{3*})_{n-1}X^*L^{2*}X^*(CR^{2*}R^{3*})_{n-1}COLv$  (IV)

(where Lv is a leaving group as defined above, optionally forming a ring by being attached to a nitrogen of an adjacent moiety $X^*$; and $R^{2*}$, $R^{3*}$, $L^{2*}$ and $X^*$ are as defined above) with a compound of formula V $HNR^{1*}—L^{1**}NR^{1*}H$  (V)

(where $R^{1*}$ is a group $R^1$ or a protected group $R^1$ and $L^{1**}$ is a group $L^{1*}$ as defined above optionally substituted by two further $NR^{1*}H$ groups) and if necessary removing any protecting groups used;

(c) reacting a compound of formula VI

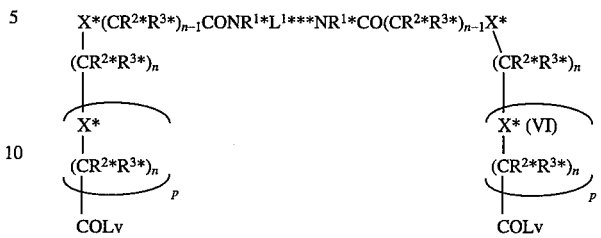

(where $L^{1***}$ is a group $L^{1*}$ as defined above, optionally substituted by a group $$-alk^*-NR^{1*}CO(CR^{2*}R^{3*})_{n-1}[X^*(CR^{2*}R^{3*})_n]_p X^*(CR^2IR^{3*})_{n-1}COLv$$

where $alk^*$ is a group alk or a protected group alk, and $R^{1*}$, $R^{2*}$, $R^{3*}$, $X^*$ and Lv are as defined above) with a compound of formula VII $HNR^{1*}—L^{1''}—NR^{1*}H$  (VII)

(where $L^{1''}$ is a group $L^{1*}$ as defined above optionally substituted by a group $-alk^*-NR^{1*}H$), and if necessary removing any protecting groups used; and (d) converting a compound of formula I into a chelate complex or salt thereof.

The compounds of formula II may be prepared in a number of ways using techniques known from the literature or analogous to literature described techniques or by using the reactions of steps (b) or (c) or analogous reactions. In particular, starting materials as described in WO-A-90/08138 may be used.

Thus for example compounds of formula I can be prepared according to the following reaction schemes:

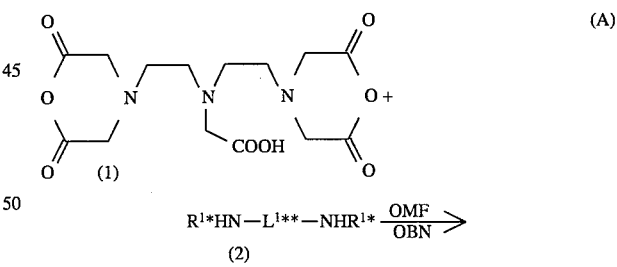
(A)

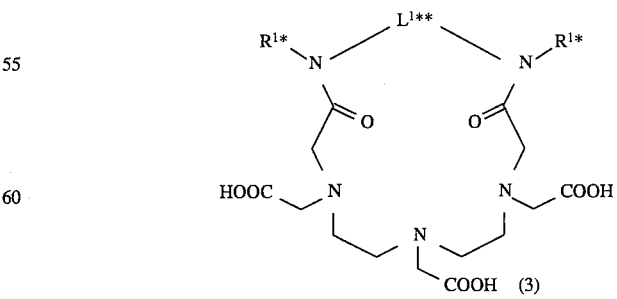

(1) + 2 (2) ⟶ (B)

11
-continued
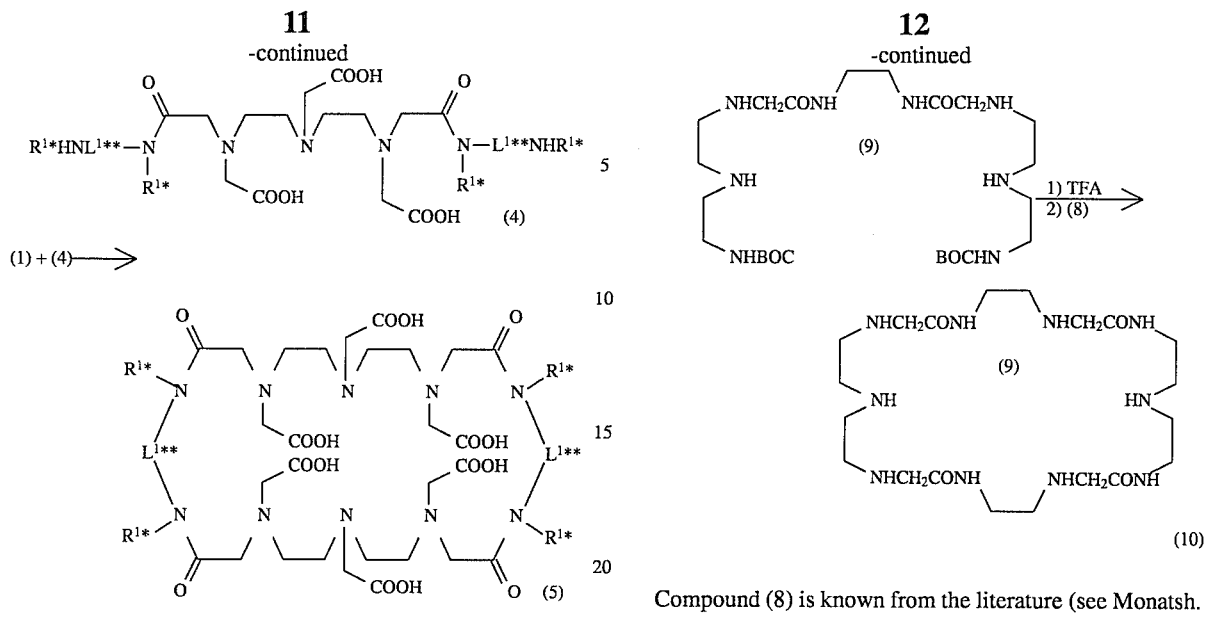
where $L^{1**}$ is for example $(CR^{2*}R^{3*})_z$ (where z is 0–6) and $R^{1*}$ is for example hydrogen
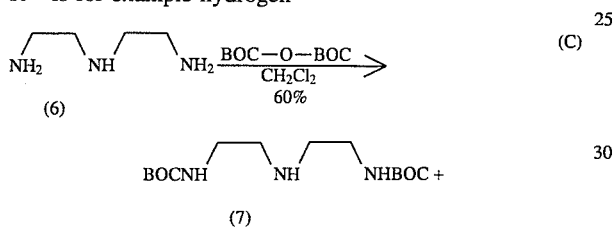
12
-continued
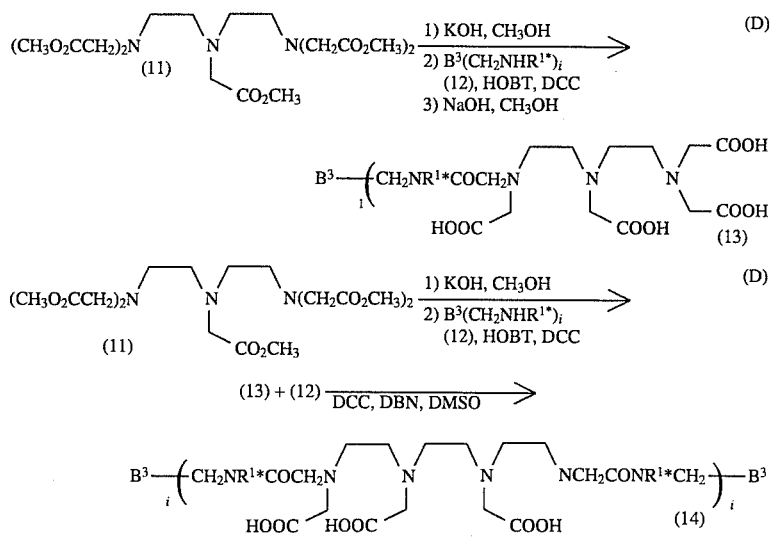
Compound (8) is known from the literature (see Monatsh. Chem. 116:217 (1985) and references herein.
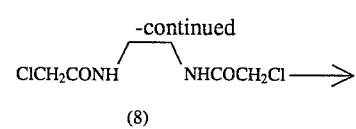
DCC=dicyclohexylcarbodiimide
DBN=1,5-diazabicyclo[4.3.0]non-3-ene where $B^3$ is spacer group, e.g. $N(CH_2)_3$, $CH(CH_2)_3$,

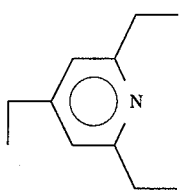

$(CH_2)_2$, $(CH_2)_3$,

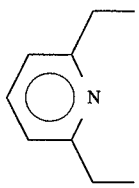

etc. and i is 2 or 3).

The end products of reaction schemes (A), (B), (C) and (D) if compounds of formula II, may be alkylated to introduce further A groups, for example by reaction with a haloalkanoate (e.g. $BrCH_2COOLi$).

Further reaction schemes for the production of compounds of formula II will be evident to the skilled chemist from the literature, e.g. Tabushi et al. Tetr. Lett. 4339 (1976) and 1049 (1977), Richmann et al. JACS 96: 2268 (1974), Nelson, Pure and Applied Chemistry 52: 461–276 (1980), Moi et al. JACS 110: 6266 (1988), EP-A-287465 (Guerbet), Stetter et al. Tetrahedron 37: 767 (1981), EP-A-232751 (Squibb), Hancock et al. JACS 110: 2788–2794 (1988), Smith et al. JACS 111: 7437–7443 (1989) and the references listed therein.

To introduce A groups into a compound of formula II, the procedure of step (a) may be effected in an aqueous, preferably basic, medium, for example by using a halocarboxylic acid or a metal, e.g. Li, salt thereof (where Hal is bromine or chlorine) followed by amidation or esterification of the carboxyl group.

The introduction of an A moiety other than a carboxylic acid residue may for example be performed as follows:

a) To introduce a phosphonic acid moiety, the general method for synthesis of alpha-aminophosphonic acids described by K. Moedritzer et al. in J. Org. Chem 31: 1603 (1966) may be used.

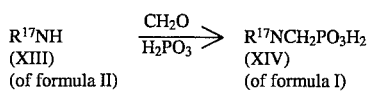

(where $R^{17}NA$ is a compound of formula I).

b) To introduce a hydroxamic acid moiety, the general method for transformation of an activated acid derivative into a hydroxamic acid described by P. N. Turowski et al. In Inorg. Chem. 27: 474 (1988) may be used.

c) To introduce a sulfonic acid moiety, synthesis may be performed by alkylation of an amino function for example with iodomethanesulfonic acid

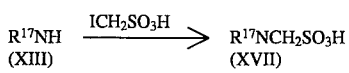

d) To introduce a nonionizing A group, synthesis may be performed by alkylation of an amino function with an optionally hydroxyl-protected alkyl (or alkoxyalkyl, hydroxyalkyl etc.) halide:

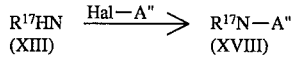

followed if necessary by deprotection, e.g. debenzylation.

Amide derivatives of formula I may be produced from the oligo acids by methods analogous to those of EP-A-250358 or of EP-A-299795. Furthermore, hydrophillic substituents on the skeleton of the chelants of formula I may be introduced by methods analogous to those of EP-A-299795.

Chelants of formula I may be used as the basis for bifunctional chelants or for polychelant compounds, that is compounds containing several independent chelant groups, by substituting for one A, $R^1$, $R^2$, $R^3$, $R^5$ or $R^6$ group a bond or linkage to a macromolecule or polymer, e.g. a tissue-specific biomolecule or a backbone polymer such as polylysine or polyethyleneimine which may carry several chelant groups and may itself be attached to be macromolecule to produce a bifunctional polychelant. Such macromolecular derivatives of the compounds of formula I and the metal chelates and salts thereof form a further aspect of the present invention.

The linkage of a compound of formula I to a macromolecule or backbone polymer may be effected by any of the conventional methods such as the carbodiimide method, the mixed anhydride procedure of Krejcarek et al. (See Biochemical and Biophysical Research Communications 77: 581 (1977)), the cyclic anhydride method of Hnatowich et al. (see Science 220: 613 (1983) and elsewhere), the backbone conjugation techniques of Meares et al. (see Anal. Biochem. 142: 68 (1984) and elsewhere) and Schering (see EP-A-331616 for example) and by the use of linker molecules as described for example by Nycomed in WO-A-89/06979.

Salt and chelate formation may be performed in a conventional manner. The chelating agents of formula I are particularly suitable for use in detoxification or in the formation of metal chelates, chelates which may be used for example in or as contrast agents for in vivo or in vitro magnetic resonance (MR), X-ray or ultrasound diagnostics (e.g. MR imaging and MR spectroscopy), or scintigraphy or in or as therapeutic agents for radiotherapy, and such uses of these metal chelates form a further aspect of the present invention.

Salts or chelate complexes of the compounds of the invention containing a heavy metal atom or ion are particularly useful in diagnostic imaging or therapy. Especially preferred are salts or complexes with metals of atomic numbers 20–32, 42–44, 49 and 57 to 83, especially Gd, Dy and Yb. For use as an MR-diagnostics contrast agent, the chelated metal species is particularly suitably a paramagnetic species, the metal conveniently being a transition metal or a lanthanide, preferably having an atomic number of 21–29, 42, 44 or 57–71. Metal chelates in which the metal species is Eu, Gd, Dy, Ho, Cr, Mn or Fe are especially preferred and $Gd^{3+}$, $Mn^{2+}$, and $Dy^{3+}$ are particularly preferred. Chelates of ions of these metals specifically listed above with chelants of formula I or their salts with physiologically tolerable counterions are particularly useful for the diagnostic imaging procedures mentioned herein and they and their use are deemed to fall within the scope of the invention and references to chelates of compounds of formula I herein are consequently to be taken to include such chelates.

For use as contrast agents in MRI, the paramagnetic metal species is conveniently non-radioactive as radioactivity is a characteristic which is neither required or desirable for MR-diagnostics contract agents. For use as X-ray or ultrasound contrast agents, the chelated metal species is preferably a heavy metal species, for example a non-radioactive metal with an atomic number greater than 37, preferably greater than 50, e.g. $Dy^{3+}$.

For use in scintigraphy and radiotherapy, the chelated metal species must of course be radioactive and any conventional complexable radioactive metal isotope, such as $^{99m}Tc$, $^{67}Ga$ or $^{111}In$ for example, may be used. For radiotherapy, the chelating agent may be in the form of a metal chelate with for example $^{153}Sm$, $^{67}Cu$ or $^{90}Y$.

For use in detoxification of heavy metals, the chelating agent should be in salt form with a physiologically acceptable counterion, e.g. sodium, calcium, ammonium, zinc or meglumine, e.g. as the sodium salt of the chelate of the compound of formula I with zinc or calcium.

Where the metal chelate carries an overall charge it will conveniently be used in the form of a salt with a physiologically acceptable counterion, for example an ammonium, substituted ammonium, alkali metal or alkaline earth metal (e.g. calcium) cation or an anion deriving from an inorganic or organic acid. In this regard, meglumine salts are particularly preferred.

Viewed from a further aspect, the present invention provides a diagnostic or therapeutic agent comprising a metal chelate, whereof the chelating entity is the residue of a compound according to the present invention, together with at least one pharmaceutical or veterinary carrier or excipient, or adapted for formulation therewith or for inclusion in a pharmaceutical formulation for human or veterinary use.

Viewed from another aspect, the present invention provides a detoxification agent comprising a chelating agent according to the invention in the form a weak complex or salt with a physiologically acceptable counterion, together with at least one pharmaceutical or veterinary carrier or excipient, or adapted for pharmaceutical formulation for human or veterinary use.

The diagnostic and therapeutic agents of the present invention may be formulated with conventional pharmaceutical or veterinary formulation aids, for example stabilizers, antioxidants, osmolality adjusting agents, buffers, pH adjusting agents, etc. and may be in a form suitable for parenteral or enteral administration, for example injection or infusion or administration directly into a body cavity having an external escape duct, for example the gastrointestinal tract, the bladder or the uterus. Thus the agent of the present invention may be in a conventional pharmaceutical administration form such as a tablet, capsule, powder, solution, suspension, dispersion, syrup, suppository, etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additional (e.g. 0.01 to 10 mole percent) of chelants (such as, for example, DTPA, DTPA-bisamide or non-complexed chelants of formula I) or calcium chelate complexes (as for example calcium DTPA, CaNaDTPA-bisamide, calcium salts or chelates of chelants of formula I), or, optionally, additions (e.g. 1 to 50 mole percent) of calcium or sodium salts (for example, calcium chloride, calcium ascorbate, calcium gluconate or calcium lactate combined with metal chelate complexes of chelants of formula I and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavouring.

For MRI and for X-ray imaging of some portions of the body the most preferred mode for administering metal chelates as contrast agents is parenteral, e.g. intravenous administration. Parenterally administrable forms, e.g. intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactates Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Where the diagnostic or therapeutic agent comprises a chelate or salt of a toxic metal species, e.g. a heavy metal ion, it may be desirable to include within the formulation a slight excess of the chelating agent, e.g. as discussed by Schering in DE-A-3640708, or more preferably a slight excess of the calcium salt of such a chelating agent.

For MRI-diagnostic examination, the diagnostic agent of the present invention, if in solution, suspension or dispersion form, will generally contain the metal chelate at concentration in the range 1 micromole to 1.5 mole per liter, preferably 0.1 to 700 mM. The diagnostic agent may however be supplied in a more concentrated form for dilution prior to administration. The diagnostic agent of the invention may conveniently be administered in amounts of from $10^{-3}$ to 3 mmol of the metal species per kilogram of body weight, e.g. about 1 mmol Dy/kg bodyweight.

For X-ray examination, the dose of the contrast agent should generally be higher and for scintigraphic examination the dose should generally be lower than for MRI examination. For radiotherapy and detoxification, conventional dosages may be used.

Viewed from a further aspect, the present invention provides a method of generating enhanced images of the human or non-human animal body, which method comprises administering to said body a diagnostic agent according to the present invention and generating an X-ray, MR, ultrasound or scintigraphic image of at least a part thereof.

Viewed from a further aspect, the present invention provides a method of radiotherapy practised on the human or non-human animal body, which method comprises administering to said body a chelate of a radioactive metal species with a chelating agent according to the invention.

Viewed from a further aspect, the present invention provides a method of heavy metal detoxification practised on the human or non-human animal body, which method comprises administering to said body a chelating agent according to the invention in the form of a weak complex or salt with a physiologically acceptable counterion.

Viewed from a yet further aspect, the present invention also provides the use of the compounds, especially the metal chelates, according to the invention for the manufacture of diagnostic or therapeutic agents for use in methods of image generation, detoxification or radiotherapy practised on the human or non-human animal body.

Viewed from a still further aspect, the present invention provides a process for the preparation of the metal chelates of the invention which process comprises admixing in a solvent a compound of formula I or a salt (e.g. the sodium salt) or chelate thereof together with an at least sparingly soluble compound of said metal, for example a chloride, oxide, acetate or carbonate.

Viewed from a yet still further aspect, the present invention provides a process for the preparation of the diagnostic or therapeutic agent of the present invention, which comprises admixing a metal chelate according to the invention, or a physiologically acceptable salt thereof, together with at least one pharmaceutical or veterinary carrier or excipient.

Viewed from a yet still further aspect, the present invention provides a process for the preparation of the detoxification agent of the invention, which comprises admixing a chelating agent according to the invention in the form of a salt with a physiologically acceptable counterion together with at least one pharmaceutical or veterinary carrier or excipient.

The disclosures of all of the documents mentioned herein are incorporated by reference.

The present invention will now be illustrated further by the following non-limiting Examples. All ratios and percentages given herein are by weight and all temperatures are in degrees Celsius unless otherwise indicated.

EXAMPLE 1

Synthesis of
1,4,7-tris(carboxymethyl)-9,14-dioxo-1,4,7,10,13-pentaazacyclopentadecane (DTPAEAM)

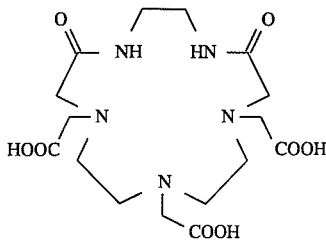

A 500 mL three-neck flask was charged with 150 mL of dry DMSO and the flask flushed with nitrogen. Two syringes were charged separately with solutions of diethylenetriaminepentaacetic acid dianhydride (2.00 g, 5.60 mmol) in 125 mL of DMSO, and 1,2-diaminoethane (0.336 g, 5,60 mmol) in DMSO/DBN (122 mL/3 mL). The solutions were added simultaneously to the flask at ambient temperature at a rate of 40 mL/hour. After the addition was complete, the reaction mixture was allowed to stir for 48 hours, concentrated under vacuum to 10 mL and 5 mL of water added. This solution, at pH 10.9, was applied to AG1-X8 (100–200 mesh, OAc⁻) resin, and the column eluted with 0.5N acetic acid to yield 0.71 g (30%) product as a white solid after acetic acid removal and lyophilization.

$^1$H NMR (D$_2$O) δ 3.0 (s, 8H), 3.20 (s, 4H), 3.40 (S, 4H), 3.50 (s, 4H), 3.50 (s, 2H), 8.35 (br s, 2H). FAB mass spectrum, m/z: 418 (MH$^+$).

EXAMPLE 2

Synthesis of
1,4,7-tris(carboxymethyl)-9,15-dioxo-1,4,7,10,14-pentaazacyclohexadecane DTPAPAM

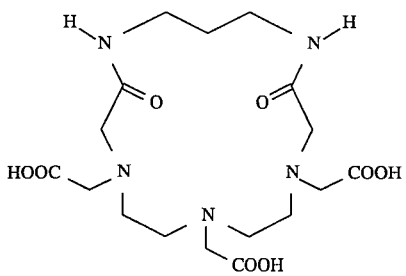

A 500 mL three-neck round bottom flask was charged with 100 mL of dry DMF and the flask flushed with nitrogen. Two syringes were charged separately with solutions of diethylenetriaminepentaacetic acid dianhydride (2.00 g, 5.60 mmol) in 175 mL of DMF and 1,3-diaminopropane (0.415 g, 5.60 mmol) in DMF/DBN (172 mL/3 mL). The two syringes, mounted on a syringe pump were connected to the flask via two long needles passing through rubber septa. These solutions were added dropwise at ambient temperature at a rate of 40 mL/hour to a vigorously stirred solution. A syringe filled with DBN remained positioned in the flask such that additional DBN could be added dropwise to the reaction mixture when cloudiness was seen. A total of 2.5 mL of additional DBN was required to maintain a homogeneous reaction mixture. After the addition was complete, the reaction mixture was allowed to stir overnight, stripped to dryness, and 1N HCl added to adjust the pH to 10.5. This solution was then applied to AG1-X8 (100–200 MESH, OAc⁻) resin and eluted with 0.5N acetic acid to yield 0.428 g (18%) of the title product, as a white solid after removal of acetic acid followed by lyophilization.

$^1$H NMR (D$_2$O) δ 1.58 (br t, 2H, 3.15 (m, 12H), 3.40 (s, 2H), 3.50 (S, 4H), 3.65 (s, 4H), 8.05 (t, 2H). FAB mass spectrum, m/z: 432 (MH$^+$), 454 (M+Na)$^+$.

EXAMPLE 3

Synthesis of
1,4,7-tris(carboxymethyl)-9,16-dioxo-1,4,7,10,15-pentaazacycloheptadecane (DTPABAM)

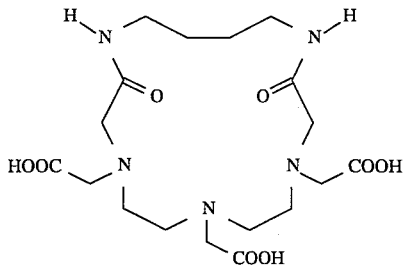

A 1 L three-neck flask was charged with 340 mL of dry DMF. Two syringes were charged separately with solutions of diethylenetriaminepentaacetic acid dianhydride (3.00 g, 8.40 mmol) in 100 mL of DMF and 1,4-diaminobutane (0.740 g, 8.40 mmol) in DMF/DBN, (96 mL/4 mL). The solutions were added simultaneously at ambient temperature to the flask at a rate of 30 mL/hour. After the addition was complete, the reaction mixture was allowed to stir overnight, stripped to dryness, and 1N HCl added to adjust the pH to 10.4. The solution was applied to AG1-X8 (100–200 mesh, OAc⁻) resin and eluted with 0.5N acetic acid to yield 0.52 g (13.6%) as a white solid, after removal of acetic acid and lyophilization.

$^1$H NMR (D$_2$O) δ 1.5 (br s, 4H), 3.02 (br s, 12H), 3.45 (s, 4H), 3.5 (s, 2H), 3.55 (s, 4H).

EXAMPLE 4

Synthesis of GdDTPABAM and Relaxivity Measurement

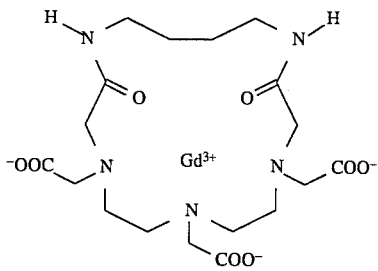

To a solution of GdCl$_2$.6H$_2$O (37.1 mg, 0.10 mmol) in 1 mL of water was added DTPABAM (44.5 mg, 0.10 mmol), and the solution was stirred until it dissolved. A pH electrode was inserted and 5M NaOH, followed by 1M NaOH, was added to adjust to pH 7.06. A xylenol orange test in MES buffer at pH 5.9 indicated free gadolinium was present. DTPABAM was added (2.56 mg) to achieve a negative test. This solution was transferred to a 5 mL volumetric flask (now 20 mM GdDTPABAM) and was used to measure the relaxivity at 10 MHz, 37° C. in water: $R_1$=4.37 mM$^{-1}$sec$^{-1}$, $R_2$=4.45 mM$^{-1}$sec$^{-1}$.

EXAMPLE 5

Synthesis of 1,4,7,16,19,22-hexakis(carboxymethyl)-9,14,24,29-tetraoxo-1,4,7,10,13,16,19,22,25,28-decaazacyclotriacontane (BisDTPAEAM)

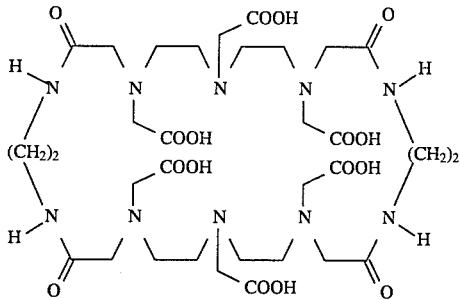

(a) Preparation of 1,1-Dimethylethyl(2-aminoethyl)carbamate((tBA)EA).

A 250 mL round bottom flask equipped with magnetic stir bar, addition funnel, and nitrogen line was charged with ethylenediamine (43 mL, 0.65 mol) and chloroform (75 mL). To the stirred solution, cooled in an ice/methanol bath, was added di-t-butyl dicarbonate (21.8 g, 0.10 mol) in 30 mL chloroform dropwise over one hour. The reaction mixture was stirred 18 hours at ambient temperature, filtered and concentrated by rotary evaporation to a clear oil. Repeated concentration from toluene (5×50 mL) provided 17 g of a colourless oil. Vacuum distillation of this oil (88°–89° C., about 3 mmHg) gave 12.1 g (76% yield) (t-BA)EA; $^1$H NMR (250 MHz, CD$_3$Cl) δ 1.12 (s, 2H), δ 1.39 (s, 9H), δ 2.74 (t, 2H, J=5.9 Hz), δ 3.11 (q, 2H, J=5.8 Hz), δ 4.97 (s, 1H).

(b) Preparation of Bis(1,1-dimethylethyl)-8,11,14-tris(carboxymethyl)-6,16-dioxo-2,5,8,11,14,17,20 -heptaazaheneicosanedioate(DTPA-bis)(tBA)EA).

A 500 mL round bottom flask equipped with magnetic stir bar and nitrogen line was charged with (tBA)EA (12.08 g, 75.42 mmol), triethylamine (15.0 mL, 107.7 mmol) and acetonitrile (200 mL). To the stirred solution was added DPTA dianhydride (12.83 g, 75.42 mmol) in one portion followed by acetonitrile (50 mL). After 15 minutes the white suspension became a colourless solution. The flask was fitted with a condenser and warmed under nitrogen in an oil bath at 50° C. After 90 hours the reaction mixture was concentrated by rotary evaporation to an off-white solid. This solid was dissolved in 150 mL DI water and concentrated by rotary evaporation to a dry solid. Residual triethylamine was removed by redissolving the solid in 150 mL DI water, adjusting the pH to 10.5 (5N NaOH), and concentrating by rotary evaporation. $^1$H NMR (250 MHz, D$_2$O): δ 1.00 (t, 8H, J=7.0 Hz), δ 1.14 (s, 18H), δ 2.86–3.00 (m, 13.4H), δ 3.06 (s, 8H), δ 3.17 (s, 4H), δ 3.32 (s, 4H), δ 3.46 (s, 2H).

(c) Preparation of 14-Imino-3-[2-[(2-aminoethyl)amino[-2-oxoethyl]-6,9 -bis(carboxymethyl)-11-oxo-3,6,9,12-tetraazatetradecanoic Acid Dihydrate (DTPA-bis(AE)A).

The DTPA-bis(tBA)EA prepared above was dissolved in 110 ml DI water, adjusted to pH 7 (5N HCl), and cooled in an ice bath. To the cool stirred solution was added concentrated HCl (39 mL) in one portion. The mixture was stirred 10 minutes in the ice bath and then for 2 hours at ambient temperature. The solution was recooled in an ice bath, titrated to pH 7 (50% NaOH), and concentrated by rotary evaporation to a dry solid (50 g). A portion of solid NaCl was removed from this material by suspending the solid in 50 mL DI water and vacuum filtering through a medium fritted glass funnel. The filtrate was adjusted to pH 2.5 (5N HCl), concentrated to a 50 mL suspension, and vacuum filtered through a coarse fritted glass funnel to remove additional solid NaCl. The filtrate was loaded onto a 9.5×2.0" (24.1× 5.1 cm) column bed of Bio-Rad AG50-X 8 (H⁺, 200–400 mesh). The column was eluted under nitrogen pressure with 0.75 L DI water followed by 1.25 L of 2N ammonium hydroxide. The product eluted with 2N ammonium hydroxide. The UV active fraction was concentrated by rotary evaporation to an oil residue. The residue was dissolved in 100 mL 1N acetic acid, concentrated by rotary evaporation, reconcentrated repeatedly from water (13×100 mL) to remove ammonium acetate, and lyophilized (10 μ, 14 hours) to afford DTPA-bis(AE)A.2H$_2$O. $^1$H NMR (250 MHz, D$_2$O/ DCl:pH 2.3): δ 2.95 (t, 4H, J=5.7 Hz), δ 3.09–3.28 (b, 8H), δ 3.35 (t, 4H, J=5.7 Hz), δ 3.51 (s, 4H), δ 3.55 (s, 2H), δ 3.66 (s, 4H).

(d) Approximately 3.0 g of DTPA-bis(AE)A.2H$_2$O was dissolved in pyridine (100 mL) and stripped to dryness. The process was repeated two more times to afford anhydrous DTPA-bis(AE)A as a free flowing off-white solid. DBN (1.58 mL, 12.8 mmol) and anhydrous DTPA-bis(AE)A (1.02 g, 2.14 mmol) were dissolved in 100 mL of DMSO, 1 mL of 4 Å molecular sieves were added, and the solution allowed to sit overnight prior to use. DTPAA (0.76309, 2.14 mmol) was dissolved in 102 mL of DMSO. The solutions were added simultaneously to a 2 L 3-neck RBF at a rate of 20 mL/hr at ambient temperature. After the addition was complete, the reaction mixture was allowed to stir for 48 hours, concentrated under vacuum to 20 mL, and 10 mL of water was added. This solution was adjusted to pH 10.7 with 5N NaOH and applied to AG1-X 8, (100–200 mesh, OAc⁻) resin, and the product eluted with 1N acetic acid to yield 0.61 g (34%) as a white solid after acetic acid removal and lyophilization. $^1$H NMR (D$_2$O): δ 3.05 (br s, 8H), 3.15 (br s, 16H), 3.52 (br s, 12H), 3.66 (s, 8H). FAB mass spectrum, m/z: 8.35.

EXAMPLE 6

Synthesis of 1,4,7,20,23,26-hexakis(carboxymethyl)-9,18,28,37-tetraoxo-1,4,7,10,17,20,23,26,29,36-decaaza-12,14,31,33-cyclooctatriacontatetrayne (DTPA-TMODA)

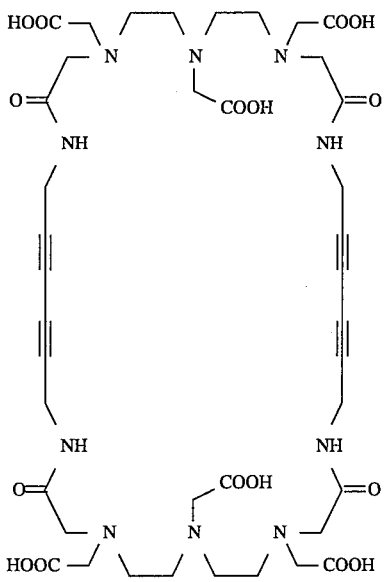

(a) Synthesis of DTPAbis(propargylamine) (DTPA-BPgA)

To a solution of propargylamine (5.0 g; 0.0908 mol) in water (35 mL) stirred at ambient temperature is added DTPA-dianhydride (6.487 g; 0.0172 mol). After stirring for 3 hours, the solution is adjusted to pH 7 using 1N HCl solution. Solvents are removed by rotary evaporation at 50° C. and the residue further dried under high vacuum at ambient temperature. Water is added to the dry residue and the solution adjusted to pH 3 with 1N HCl. Crystals which form are isolated by suction filtration, washing with water. The precipitation process is repeated if necessary.

b. Synthesis of DPTA-TMODA

DTPA-BPgA is first protected as the trimethyl ester. To a suspension of DTPA-BPgA in methanol is bubbled anhydrous hydrogen chloride gas for 20 mins. When the HCl salt has dissolved, trimethylorthoformate is added in a dropwise fashion and the solution heated under reflux for 5 hours. The reaction mixture is cooled and solvent removed by rotary evaporation. Dichloromethane is added to the system followed by sodium bicarbonate solution. The organic layer is removed via a separating funnel and the aqueous phase further extracted with dichloromethane. The combined organic fractions are washed with saline, prior to removal of organic solvent. The product is then purified by silica gel chromatography.

The macrocyclic end product is produced using copper (II) acetate in pyridine according to the method of G. Eglington and W. McCrae "The Coupling of acetylenic compounds", Adv. Org. Chem. 4: 225–328 (1963)

The free acid may be worked up from the hexamethyl ester by reaction with aqueous sodium hydroxide.

EXAMPLE 7

Synthesis of 1,4,7-tris(carboxymethyl)-9,16-dioxo-1,4,7,10,15-pentaaza-cis-12-cycloheptadecene (DTPAcis$^{C=C}$BAM)

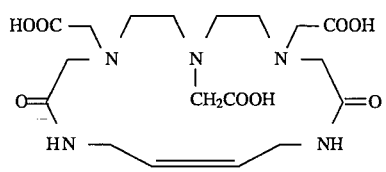

(a) Preparation of 1,4-bisphthalimido-cis-2-butene

Potassium phthalimide (63g, 0.34 mmol) was suspended in 200 mL of DMF and brought to 50° C. 1,4-dichloro-cis-2-butene (12.5 g, 0.10 mmol, 10.52 mL) was added dropwise over 3 hours while maintaining the temperature between 50° and 55° C. The mixture was heated at 60° C. for 5 hours and stirred for a further 15 hours at room temperature. The mixture was then poured into 400 mL of ice water, stirred for 10 minutes and filtered. The white filter cake was washed with 100 mL of 1% NaHCO$_3$, 50 mL H$_2$O, and dried. Recrystallization from EtOH/CH$_3$CN yielded 27 g (78%) of the bis-phthalimide as a white solid; $^1$H NMR (250 MHz, CDCl$_3$): δ 4.53 (d, 4H, 5.8 Hz), δ 5.66 (t, 2H, 5.8 Hz), δ 7.67 (t, 4H, 2.4 Hz), δ 7.80 (t, 4H, 2.5 Hz).

(b) Preparation of 1,4-diamino-cis-2-butene dihydrochloride 1,4,bisphthalimido-cis-2-butene (20.0 g, 0.058 mol) was refluxed in ethanol (125 mL). Slowly, over 0.5 hour, a solution of hydrazine monohydrate (6.37 mL, 0.130 mol) in 7 mL of water was added. The solution was then refluxed for an additional 3 hours and stirred overnight at ambient temperature. The mixture was brought to pH 1 by the slow dropwise addition of 10N HCl, stirred for 0.5 hour and allowed to sit overnight. Water (100 mL) was added, a chalky white solid filtered out, and the filtrate stripped to yield an orange-yellow solid. Recrystallization from methanol yielded 7.15 g (78%) of the diamine dihydrochloride salt; $^1$H NMR (250 MHz, D$_2$O): δ 3.54 (d, 4H, J=5.26 Hz), δ 5.67 (t, 2H, J=5.26 Hz).

(c) A 2 L three-neck flask was charged with 800 mL of DMF. Two syringes were charged separately with solutions of diethylenetriaminepentaacetic acid dianhydride (2.0 g, 5.59 mmol) in 100 mL DMSO and 1,4-diamino-cis-2-butene dihydrochloride (0.89 g, 5.59 mmol) in DMF (95.5 mL)/ DBN (4.5 mL). The solutions were added simultaneously at ambient temperature, to the flask at a rate of 8 mL/hour. After the addition was complete the reaction mixture was allowed to stir for 3 days, the volume reduced to 50 mL and 6N HCl added to adjust the pH to 10.5. The solution was applied to AG1X-8 (100–200 mesh, acetate form) resin and the product eluted with 0.5N acetic acid to yield 750 mg (32%) as a white solid, following removal of acetic acid and lyophilization. $^1$H NMR (D$_2$O): δ 2.97 (br t, 4H, J=5 Hz), δ

3.35 (s, 4H), δ 3.59 (s, 2H), 3.72 (d, 4H, J=Hz), 5.47 (t, 2H, J=5 Hz).

EXAMPLE 8

Synthesis of 1,4,7-tris(carboxymethyl)-9,12-dioxo-1,4,7,10,11-pentaazacyclotridecane (DTPAHZM) (hydrazide macrocycle)

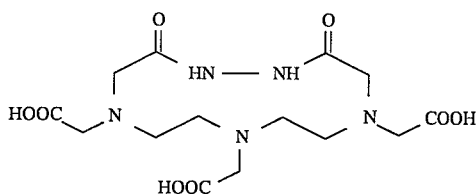

A 500 mL three-neck flask is charged with 150 mL of dry DMSO and flushed with nitrogen. Two syringes are charged separately with solutions of diethylenetriaminepentaacetic acid dianhydride (2.82 g, 7.89 mmol) and DBN (2.94 g, 2.92 mL, 23.67 mmol) in 122 mL of DMSO and anhydrous hydrazine (0.25 g, 0.25 mL, 7.89 mmol) in 125 mL DMSO. The two solutions are added simultaneously at the rate of 40 mL/hour to the flask at ambient temperature, employing a syringe pump. After the completion of addition the reaction mixture is stirred for 48 hours, concentrated under vacuum to 10 mL, and water (10 mL) is added. The solution at pH 10.5 is applied to AGIX-8 (100–200 mesh, acetate form) resin and the column is eluted with 1N acetic acid. The product is obtained by removal of acetic acid, followed by lyophilization.

EXAMPLE 9

Synthesis of 1,4,7,14,20-hexakis(carboxymethyl)-9,12,22,25-tetraoxo-1,3,7,10,11,14,17,20,23,24-decaazacyclohexacosane (DTPA-HZM)$_2$ (bis DTPA hydrazide macrocycle)

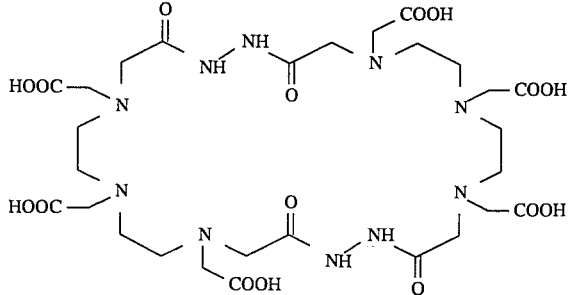

(a) Synthesis of DTPA (boc-hydrazide)$_2$

A 500 mL flask, equipped with a magnetic stir bar, reflux condenser and nitrogen line, is charged with t-butyl carbazate (0.78 g, 5.88 mmol), DTPA dianhydride (1.00 g, 2.8 mmol) and triethylamine (0.85 g, 1.18 mL, 0.4 mmol). To the mixture acetonitrile (20 mL) is added, and the heterogeneous mixture is heated at 58° C. in an oil bath. After 5 minutes a clear solution results. The reaction is allowed to proceed for 72 hours, solvent is removed by rotary evaporation yielding 2.13 g of the crude triethylammonium salt of DTPA (BOC-hydrazide)$_2$ as a white solid.

$^1$H NMR (D$_2$O): 1.04(t), 1.22(s), 2.88(m), 2.95(q); 3.16(m), 3.24(m); 3.31(s), 3.39(s); 3.59(s), 3.62(s)

The product is dissolved in 50 mL deionized water and concentrated by rotary evaporation to a dry solid. The solid is redissolved in 50 mL deionised water and the pH adjusted to 10.5 with 5N NaOH. Concentration by rotary evaporation is carried out to remove the residual triethylamine.

(b) Preparation of DTPA(hydrazide)$_2$

The DTPA (Boc-hydrazide$_2$) prepared above is dissolved in 20 mL DI water and adjusted to pH 7 with 5N HCl. It is cooled in an ice bath and stirred. To this mixture concentrated HCl (5 mL) is added in one portion. The mixture is stirred at 0° C. for 10 minutes, and then at ambient temperature for 2 hours. The solution is cooled to 0° C. in an ice bath, neutralized to pH 7 with 5N NaOH and concentrated by rotary evaporation to a dry solid. The solid is suspended in H$_2$O (5 mL) and vacuum filtered through a medium fritted glass funnel. The filtrate is adjusted to pH 2.5 (5N HCl), concentrated to a 5 mL suspension and vacuum filtered through a coarse fritted glass funnel to remove more solid NaCl. The filtrate is loaded on to Bio-Rad AG50X-8 (H$^+$form, 200–400 mesh) resin, washed with 1 L of deionized water and eluted with 2N ammonium hydroxide. The fraction containing the product is concentrated by rotary evaporation, treated with 1N acetic acid (10 mL) and concentrated again. Repeated treatment with water (10×10 mL) and reconcentration are carried out to remove ammonium acetate, and the DTPA(HZ)$_2$ is recovered by lyophilization.

(c) Preparation of (DTPA-HZM)$_2$

The product DTPA(HZ)$_2$ obtained above is treated with pyridine (3×10 mL) and concentrated to dryness to yield the anhydrous DTPA(HZ)$_2$ as a free flowing solid. DBN (2.47 g, 2.46 mL, 19.92 mmol) and DTPA(HZ)$_2$ (1.40 g, 3.32 mmol) are dissolved in 100 mL DMSO and the solution is dried by allowing it to stand overnight with 1 g molecular sieves (4 Å). A solution of DTPA bisanhydride (1.19 g, 3.32 mmol) in 100 mL dry DMSO is treated similarly. The two solutions are added simultaneously to a 2 L 3-neck round-bottom flask containing 1 L dry DMF under nitrogen, at the rate of 40 mL/hour, at ambient temperature. The reaction mixture is then stirred at ambient temperature for 48 hours, concentrated to 20 mL, and 20 mL deionized H$_2$O is added. The pH of the solution is adjusted to 10.5 with 5N NaOH, and it is applied to AG1X-8 (100–200 mesh, acetate form) resin. The product is eluted with 1N acetic acid and the eluate is concentrated. The residue is repeatedly treated with water (3×50 mL) and concentrated to remove acetic acid. (DTPA-HZM)$_2$ is obtained as a white solid after lyophilization.

We claim:

1. A chelating agent of formula I

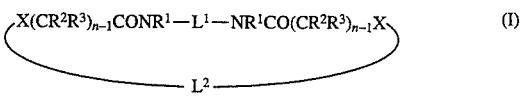

wherein L$^1$ represents a bond or an optionally unsaturated C$_{2-14}$ hydrocarbon chain optionally substituted by groups selected from R$^2$, R$^3$ and R$^4$, optionally having chain backbone methylene moieties which are separated by at least 2 ring carbon atoms from ring heteroatoms replaced by oxygen or sulphur atoms or NA' groups, optionally carrying a fused 5–8 membered saturated or unsaturated carbocyclic or heterocyclic ring itself optionally substituted by groups selected from R$^2$, R$^3$ and R$^4$, and optionally carrying a fused macrocyclic ring of formula Ia

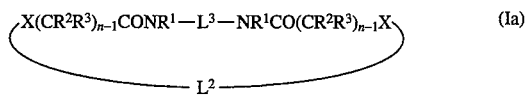

wherein $L^1$ and $L^3$ share at least two common ring atoms and optionally an unsaturated ring bond and $L^3$ is as defined for $L^1$ but may not itself carry a further fused macrocycle of formula Ia;

$L^2$ represents a group of formula $[(CR^2R^3)_nX]_m(CR^2R^3)_n$ optionally having a moiety $[(CR^2R^3)_nX]_2(CR^2R^3)_n$ replaced by a moiety $(CR^2R^3)_{n-1}CONR^1\text{-}L^4\text{-}NR^1CO(CR^2R^3)_{n-1}$ where $L^4$ is a group $L^1$ but may not carry a fused macrocycle of formula Ia;

$R^4$ groups on separate L groups together represent a group of formula Ib

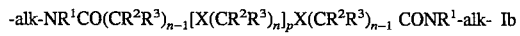

-alk-$NR^1CO(CR^2R^3)_{n-1}[X(CR^2R^3)_n]_pX(CR^2R^3)_{n-1}$ $CONR^1$-alk- Ib where alk is a group $L^1$ but may not carry a fused macrocycle of formula Ia or a substituent $R^4$;

each $R^1$ independently represents a group $R^5$ or $X^2R^5$ where $X^2$ represents an oxygen or sulphur atom or a group $NR^5$ and each $R^5$ independently represents a hydrogen atom or an alkyl or aryl group optionally substituted by a group Y;

each X independently represents an oxygen or sulphur atom or, preferably, a group of formula NA;

each A independently represents a hydrogen atom or an alkyl group optionally substituted by a group Y;

each A' independently represents a group A or a group $R^4$;

each Y independently represents a group Z, COX, $SO_2Z$, $POZ_2$, $CON(OR^6)R^6$ or CSZ;

each Z independently represents a group $OR^6$, $SR^6$ or $NR_2^6$;

each $R^6$ independently represents a hydrogen atom or an alkyl group optionally carrying at least one substituent selected from hydroxyl and alkoxy groups, or $NR_2^6$ together represents a nitrogen-attached 5–7 membered saturated heterocyclic ring optionally containing as a further ring heteroatom a nitrogen, oxygen or sulphur atom and optionally substituted by one or more $R^7$ groups;

each $R^7$ independently represents a halogen atom, a hydroxy or sulphonate group or an alkyl or alkoxy group optionally carrying at least one or more hydroxy, alkoxy or hydroxyalkyl groups;

each $R^2$ and $R^3$ independently represents a hydrogen atom or an aryl or alkyl group optionally carrying at least one substituent selected from aryl and Y groups, or two groups A and/or $R^3$ attached at different positions on a macrocyclic ring may together with the intervening macrocyclic ring atoms form a independently represents 5–8 membered saturated or unsaturated heterocyclic or carbocyclic ring, itself optionally substituted by one or more $R^7$ group;

m is an integer of 0–8;
n is an integer of 2–5;
p is an integer of 0–8;
with the proviso that at least 2 ionizable Y groups are present or a chelate complex or salt thereof wherein heterocyclic ring, unless otherwise specified, means a ring containing at least one heteroatom selected from the group consisting of nitrogen, oxygen or sulfur.

2. A chelating agent as claimed in claim 1 of formula Ic, Id, Ie of If

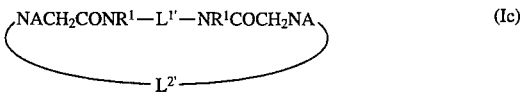

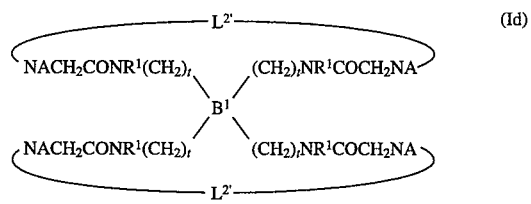

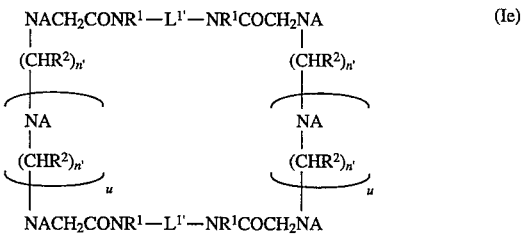

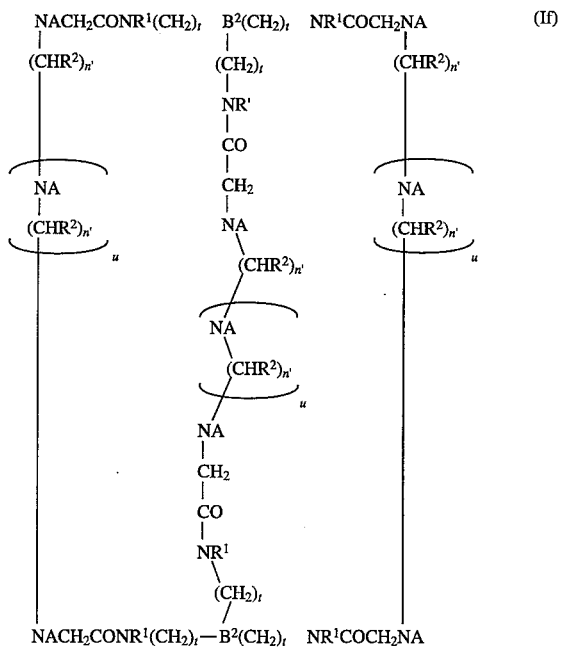

(wherein $L^{1'}$ is a $C_{2-10}$ alkylene, alkenylene, alkynylene, oxaalkylene or azaalkylene group optionally substituted by a hydrophillic group and optionally carrying a fused 5 to 6 membered saturated or unsaturated homo- or heterocyclic ring which ring if heterocyclic contains one or two non-adjacent ring heteroatoms selected from O, N and S;

$L^{2'}$ is a group of formula $[(CHR^2)_{n'}X]_m(CHR^2)_{n'}$;

each n' is 2 or 3;

each t is 1, 2 or 3;

each u is 0, 1 or 2;

$B^1$ is a quadrivalent branching group selected from alkanetetrayl and alkenetetrayl groups and carbon-attached 6-membered saturated or unsaturated homo or heterocyclic rings which rings if heterocyclic contain one or two non-adjacent ring heteroatoms selected from O, N and S;

$B^2$ is a trivalent branching group selected from $CR^2$, N and carbon attached 6-membered saturated or unsaturated homo or heterocyclic rings which rings if heterocyclic contain one, two or three non-adjacent ring heteroatoms selected from O, N and S;

each $R^2$ is independently hydrogen or an alkyl group optionally carrying at least one Z substituent;

and X, A, m and $R^1$ are as defined in claim 1) or a chelate complex or salt thereof.

3. A chelating agent as claimed in either of claims 1 and 2 being of formula Ig

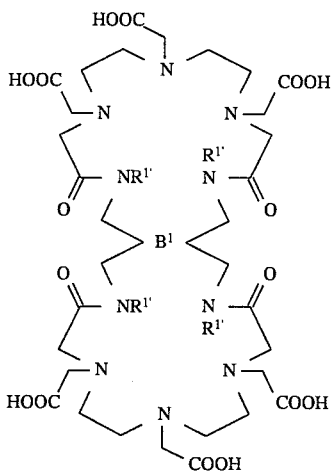

(Ig)

(wherein $R^{1'}$ is H, alkyl, or alkoxy or aryloxy; $L^{1'}$ is a 4,4,5,5-tetramethylocta-2,6-diynediyl, ethylene, trimethylene, tetramethylene, or but-2-enediyl group optionally substituted by a hydrophillic group; $B^1$ is >CH—CH< or >C=C< and $L^{1'}$ is an ethylene, trimethylene or tetramethylene group or a group of formula

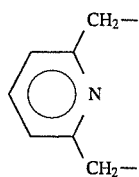

optionally substituted by a hydrophillic group) and the metal chelates and salts and esters thereof.

4. A chelating agent as claimed in either of claims 1 and 2 being of formula Ih

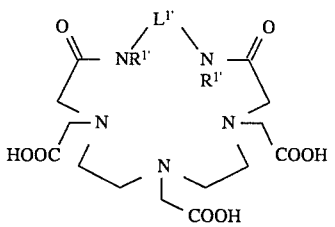

(Ih)

(wherein $R^{1'}$ is H, alkyl, or alkoxy or aryloxy, $L^{1'}$ is a 4,4,5,5-tetramethylocta-2,6-diynediyl, ethylene, trimethylene, tetramethylene, or but-2-enediyl group optionally substituted by a hydrophillic group; $B^1$ is >CH—CH< or >C=C< and $L^{1'}$ is an ethylene, trimethylene or tetramethylene group or a group of formula

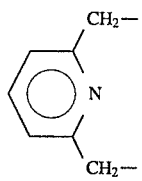

optionally substituted by a hydrophillic group) and the metal chelates and salts and esters thereof.

5. A chelating agent as claimed in either of claims 1 and 2 being of formula Ij

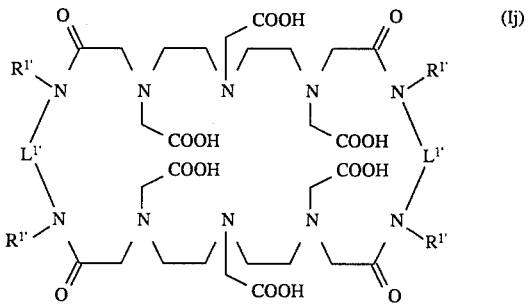

(Ij)

(wherein $R^{1'}$ is H, alkyl, or alkoxy or aryloxy, $L^{1'}$ is a 4,4,5,5-tetramethylocta-2,6-diynediyl, ethylene, trimethylene, tetramethylene, or but-2-enediyl group optionally substituted by a hydrophillic group; $B^1$ is >CH—CH< or >C=C< and $L^{1'}$ is an ethylene, trimethylene or tetramethylene group or a group of formula

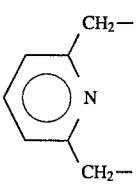

optionally substituted by a hydrophillic group) and the metal chelates and salts and esters thereof.

6. A chelating agent as claimed in any one of claims 2 to 5 selected from the group consisting of:

1,4,7-tris(carboxymethyl)-9,14-dioxo-1,4,7,10,13-pentaazacyclopentadecane;

1,4,7-tris(carboxymethyl)-9,15-dioxo-1,4,7,10,14-pentaazacyclohexadecane;

1,4,7-tris(carboxymethyl)-9,16-dioxo-1,4,7,10,15-pentaazacycloheptadecane;

1,4,7,16,19,22-hexakis(carboxymethyl)-9,14,24,29-tetraoxo-1,4,7,10,13,16,19,22,25,28-decaazacyclotriacontane;

1,4,7,20,23,26-hexakis(carboxymethyl)-9,18,28,37-tetraoxo-1,4,7,10,17,20,23,26,29,36-decaaza- 12,14,31, 33-cyclotriacontatetrayne;

1,4,7-tris(carboxymethyl)-9,16-dioxo-1,4,7,10,15-pentaaza-cis-12-cycloheptadecene;

1,4,7-tris(carboxymethyl)-9,12-dioxo-1,4,7,10,11-pentaazacyclotridecane; and 1,3,7,14,20-hexakis(carboxymethyl)-9,12,22,25-tetraoxo-1,3,7,10,11,14,17,20,23,24-decaazacyclohexacosane;

or a chelate complex or salt or ester thereof.

7. A compound as claimed in any one of claims 1 to 6 being a paramagnetic metal ion chelate complex of a said chelating agent.

8. A diagnostic or therapeutic agent comprising a metal chelate, whereof the chelating entity is the residue of a chelating agent as claimed in any one of claims 1 to 7, together with at least one pharmaceutical or veterinary carrier or excipient.

9. A method of generating enhanced images of the human or non-human animal body, which method comprises administering to said body a diagnostic agent as claimed in claim 8 and generating an X-ray, MR, ultrasound or scintigraphic image of at least a part.

* * * * *

UNITED STATES PATENT AND TRADEMARK OFFICE
CERTIFICATE OF CORRECTION

PATENT NO. : 5,556,968   Page 1 of 3
DATED : September 17, 1996
INVENTOR(S) : Joan F. Carvalho, et al It is certified that error appears in the above-identified patent and that said Letters Patent is hereby corrected as shown below:

Col. 1, line 20, after "aminopoly", insert -- - --.

Col. 2, line 56, replace "COHN$^1$" with --CONR$^1$--.

Col. 4, line 55, replace "caries" with --carries--.

Col. 7, line 66, replace "morpholine" with --morpholino--.

Col. 9, line 54, replace "reaction" with --reacting--.

Col. 10, line 19 replace "(CR$^2$IR$^{3'}$)" with --(CR$^{2'}$R$^{3'}$)--.

Col. 12, line 22, replace "herein" with --herein)--.

Col. 13, line 55, replace "In" with --in--.

Col. 14, line 18, replace "to" with --a--; and replace "bifunctional polychelant." with --bifunctional-polychelant--.

UNITED STATES PATENT AND TRADEMARK OFFICE
CERTIFICATE OF CORRECTION

PATENT NO.  : 5,556,968
DATED       : September 17, 1996
INVENTOR(S) : Joan F. Carvalho, et al It is certified that error appears in the above-identified patent and that said Letters Patent is hereby corrected as shown below:

Col. 14, line 55, replace "$Mr^{2+}$", with --$Mn^{2+}$, $Fe^{3+}$--

Col. 16, line 21, replace "Lactates" with --Lactated--.

Col. 16, line 40, replace "liter" with --litre--.

Col. 17, line 58, replace "5,60" with --5.60--.

Col 18, line 40, replace "MESH" with --mesh--.

Col. 18, line 44, replace "(br t, 2H," with --(br t, 2H),--.

Col. 19, line 31, replace "$GdCl_2$" with --$GdCl_3$--.

Col. 20, line 8, replace "$CD_3Cl$)" with --$CD_3Cl$):--

Col. 20, line 32, replace "amino[" with --amino]--.

Col. 21, line 57, replace "DPTA" with --DTPA--.

Col. 22, line 31, replace "50°" with --50--.

Col. 23, line 58, replace "500" with --100--.

UNITED STATES PATENT AND TRADEMARK OFFICE
CERTIFICATE OF CORRECTION

PATENT NO. : 5,556,968
DATED : September 17, 1996
INVENTOR(S) : Joan F. Carvalho, et al It is certified that error appears in the above-identified patent and that said Letters Patent is hereby corrected as shown below:

Col. 25, line 55, delete "indepentently represents".

Col. 26, line 55, replace "to" with --or--.

Col. 27, line 63, replace "or aryloxy," with --or aryloxy;--.

Col. 28, line 26, replace "or aryloxy," with --or aryloxy;--.

Col. 28, line 42, replace "2" with --1--.

Col. 28, line 56, replace "33-cyclotriacontatetrayne" with --33 cyclooctatriacontatetrayne--.

Col. 28, line 61, replace "3" with --4--.

Signed and Sealed this

Twentieth Day of July, 1999

Attest:

Q. TODD DICKINSON

*Attesting Officer*            *Acting Commissioner of Patents and Trademarks*